United States Patent [19]
Wood, Sr. et al.

[11] Patent Number: 5,800,344
[45] Date of Patent: Sep. 1, 1998

[54] VIDEO LARYNGOSCOPE

[75] Inventors: Robert J. Wood, Sr., Syracuse; Connie R. Walts, Auburn; Michael Lynch, Skaneateles, all of N.Y.

[73] Assignee: Welch Allyn, Inc., Skaneateles Falls, N.Y.

[21] Appl. No.: 736,031

[22] Filed: Oct. 23, 1996

[51] Int. Cl.⁶ ..................................... A61B 1/26
[52] U.S. Cl. ..................... 600/188; 600/185; 600/196
[58] Field of Search ........................ 600/185, 188, 600/189, 190, 196, 160, 163, 164, 167, 176, 182

[56] References Cited

U.S. PATENT DOCUMENTS

| | | | |
|---|---|---|---|
| 3,884,222 | 5/1975 | Moore | 600/188 |
| 4,491,865 | 1/1985 | Danna et al. . | |
| 4,651,202 | 3/1987 | Arakawa . | |
| 4,677,471 | 6/1987 | Takamura et al. . | |
| 4,736,734 | 4/1988 | Matsuura et al. . | |
| 4,877,016 | 10/1989 | Kantor et al. . | |
| 4,878,485 | 11/1989 | Adair | 128/6 |
| 4,901,708 | 2/1990 | Lee | 128/11 |
| 4,918,521 | 4/1990 | Yabe et al. . | |
| 4,989,586 | 2/1991 | Furukawa . | |
| 5,363,838 | 11/1994 | George . | |
| 5,363,839 | 11/1994 | Lankford . | |
| 5,408,992 | 4/1995 | Hamlin et al. . | |
| 5,494,483 | 2/1996 | Adair . | |
| 5,527,261 | 6/1996 | Monroe et al. . | |

*Primary Examiner*—Beverly M. Flanagan
*Attorney, Agent, or Firm*—Wall Marjama & Bilinski

[57] ABSTRACT

The invention is a laryngoscope having an image sensor assembly mounted thereto for providing video imaging of a patient's airway passage. The laryngoscope includes a distal end having a tip adapted for contact with tissue of an airway passage and an image sensor assembly mounted to a convex surface of the laryngoscope body so that an image sensor of the assembly is angled away from a tissue contacted by the tip when the laryngoscope is in use. In one embodiment, the image sensor assembly is slidably mounted on a track formed on a curved section of a laryngoscope body so that sliding of the image sensor assembly along the track adjusts the distance of the assembly from a target, and further adjusting the orientation angle of the image sensor assembly.

9 Claims, 3 Drawing Sheets

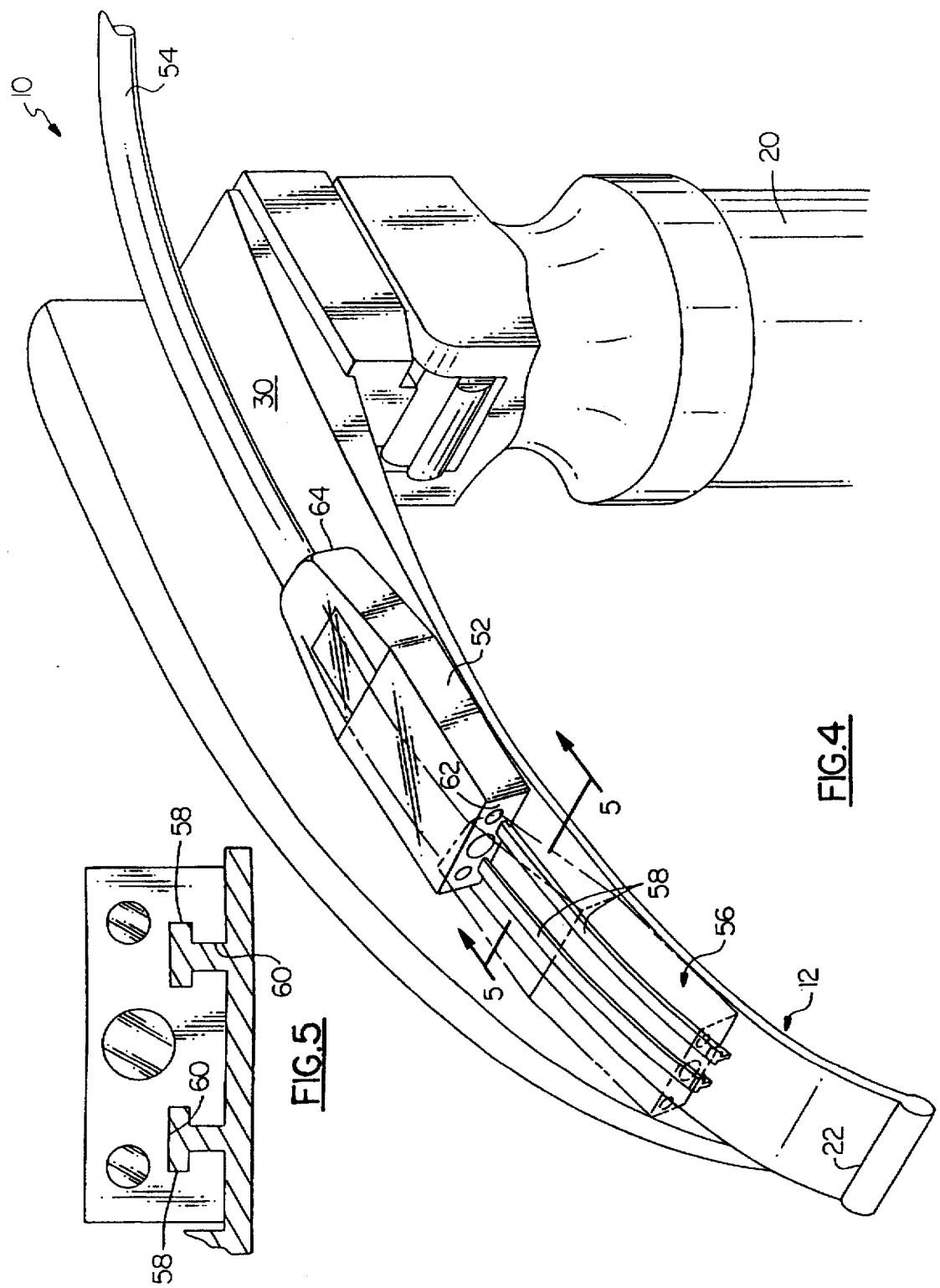

VIDEO LARYNGOSCOPE

BACKGROUND OF THE INVENTION

1. Field of the Invention

The invention relates to medical devices in general and in particular to a laryngoscope adapted to provide video imaging of an airway passage.

2. Background of the Prior Art:

In a process known as "intubation" wherein an endotracheal (breathing) tube is inserted into a patient's airway passage and through patients' pharynx, larynx, and trachea to facilitate breathing, it is common to open a patient's airway passage as wide as possible to allow unobstructed insertion of the tube.

A medical device known as a laryngoscope is typically used to accomplish such airway passage opening. A laryngoscope is a rigid or semirigid and normally curved structure having a smooth tip adapted to contact tissue of a patient's airway passage. Laryngoscope often have a guide surface for guiding entry of a breathing tube through an airway passage.

Despite the use of a laryngoscope in widening a patient's airway passage, and in guiding entry of a endotracheal breathing tube, inserting a breathing tube into a patient's airway passage is a process fraught with complication given that it is difficult to monitor the location of a breathing tube in an airway passage as it is being inserted. As a result, breathing tubes are commonly not inserted correctly through a patient's pharynx, larynx, and trachea.

To aid in the visualization of an airway passage during intubation, U.S. Pat. No. 5,363,838 to George teaches a system which uses both a laryngoscope and an "intubation facilitating scope" (normally provided by a soft malleable tube having an image sensor mounted at its distal end) in providing improved viewing of an airway passage during intubation. According to the teachings of George, an airway passage is best visualized during the intubation process, by utilizing a conventional laryngoscope to open an airway passage, and to simultaneously insert in the airway an "intubation facilitating scope" to provide imaging of the region of interest.

SUMMARY OF THE INVENTION

According to its major aspects and broadly stated the present invention is a laryngoscope adapted to provide video imaging of a patient's airway passage during use of the laryngoscope.

A laryngoscope according to the invention includes a distal end and a proximal end. The distal end includes a generally smoothed tip adapted for contact with a sensitive tissue of a patient's airway passage, and a proximal end normally adapted to receive a handle.

The elongated body of a laryngoscope according to the invention normally includes at least one elbow or is gradually curved throughout its length to define a convex surface of the laryngoscope and a concave surface of the laryngoscope.

In accordance with one embodiment of the invention, an image sensor assembly is mounted on the convex surface of the laryngoscope body and is spaced apart from the distal end (contact surface) of the laryngoscope. It will be recognized that the image sensor of an image sensor assembly mounted in this way will be directed in a direction away from the tissue being contacted and toward a region of interest when the laryngoscope is in use and in contact with tissue of an airflow passage.

Accordingly, the image sensor assembly includes an image sensor whose active surface is preferably directed in a direction generally perpendicular with the surface of the laryngoscope housing on which the assembly is mounted, a lens system for focusing images onto the image sensor, illumination elements normally provided by a fiberoptic bundles, and may include a circuit board including circuit components for preliminary processing image signals generated by the image sensor.

In accordance with another embodiment of the invention, a track is formed on the convex surface of the laryngoscope body, and a housing which houses an image sensor assembly is adapted to be received on the track. In this embodiment, the distance of the image sensor to a target object is adjusted by moving the image sensor assembly back or forth along the track.

If the track is formed along an elbow or along a curved surface of a laryngoscope body, and an image sensor assembly housing is complementarily formed so that it is received by the track, then movement of the image sensor assembly housing along the track first adjusts the distance between an image sensor and second adjusts the orientation direction of the image sensor and therefore the view field of the image sensor.

BRIEF DESCRIPTION OF THE DRAWINGS

In the drawings, wherein like numerals are used to indicate the same elements throughout the views.

FIG. 4 is a perspective view of a laryngoscope according to the invention having a detachably attached and adjustable positioned image sensor assembly;

FIG. 5 is a cross-sectional view taken along line 5—5 of FIG. 4 showing a track attachment formation for attaching an image sensor assembly housing to a laryngoscope body.

DETAILED DESCRIPTION OF THE PREFERRED EMBODIMENTS

Figure 1:
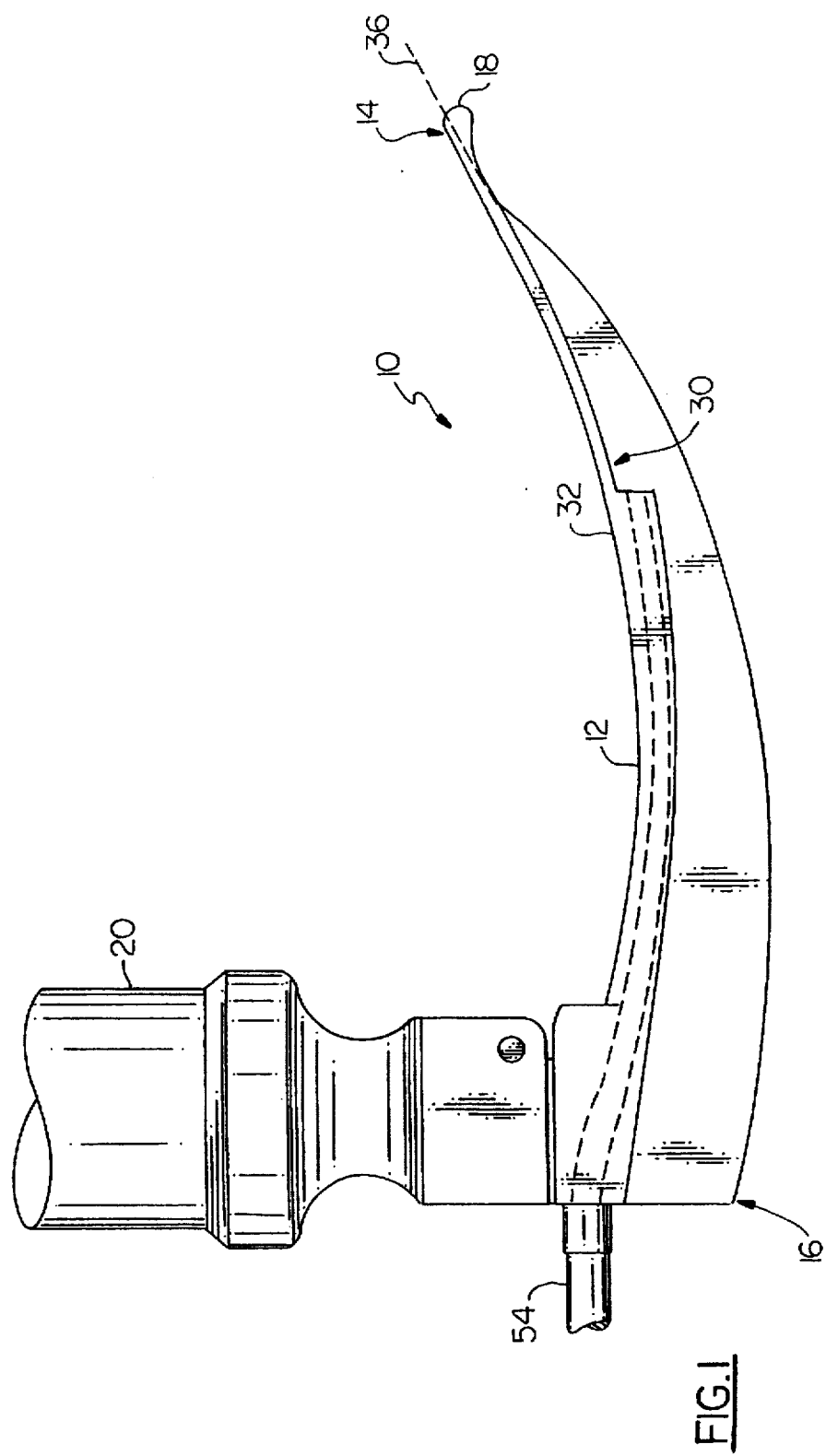
FIG. 1 is a side view of a laryngoscope according to the invention.

A laryngoscope according to the invention is shown in FIGS. 1–4. Laryngoscope 10 includes body 12 having a distal end 14 and a proximal end 16. The distal end may includes a generally smoothed tip 18 adapted for contact with a sensitive tissue of a patient's airway passage, and a proximal end 16 normally adapted to receive a handle 20. Handle 20 can be formed as a permanent part of laryngoscope 10. As seen in FIG. 4 smooth tip 18 can be formed by bending an end of body backward on itself so that end 22 contacts body 12 at spaced apart distance from smooth tip 18. Smooth tip 18 can be formed by other manufacturing processes as well. For example, a mold for metal of polymer manufacture of body 12 can include a cavity resulting in a smooth surface at tip 18 when the molding process is complete.

Figure 2:
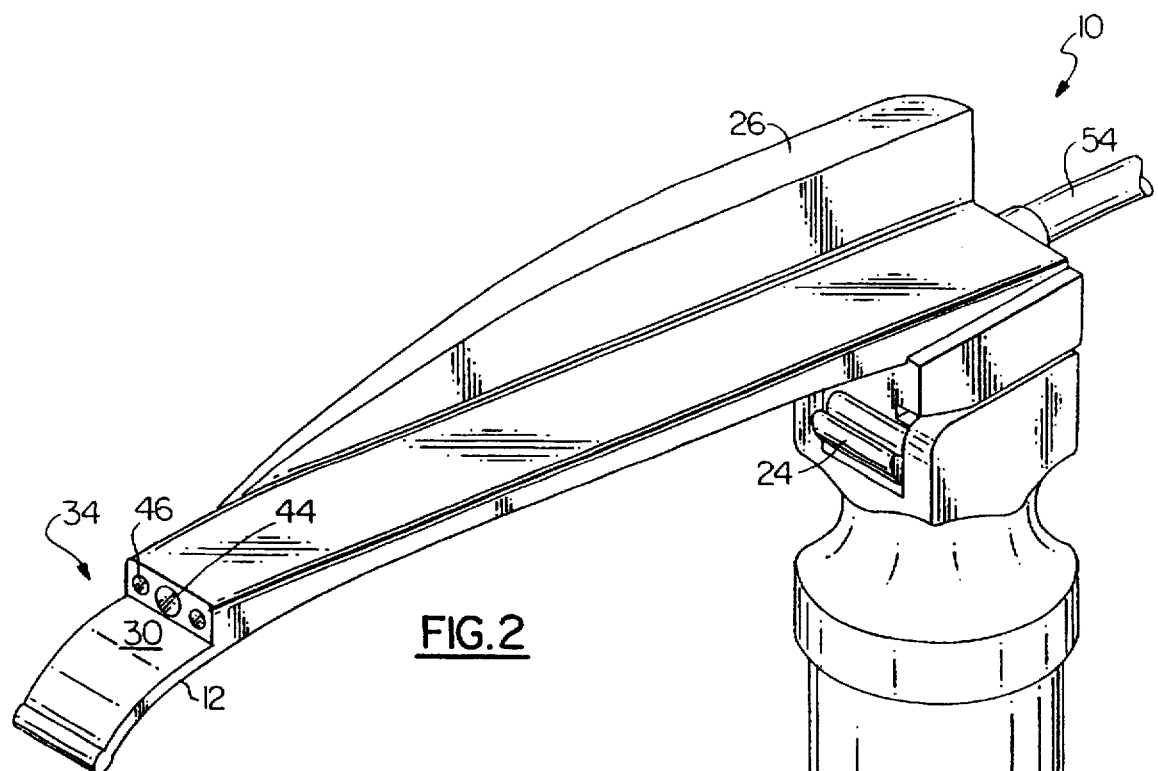
FIG. 2 is a perspective view of a laryngoscope according to the invention having a fixed position image sensor assembly.
Figure 3:
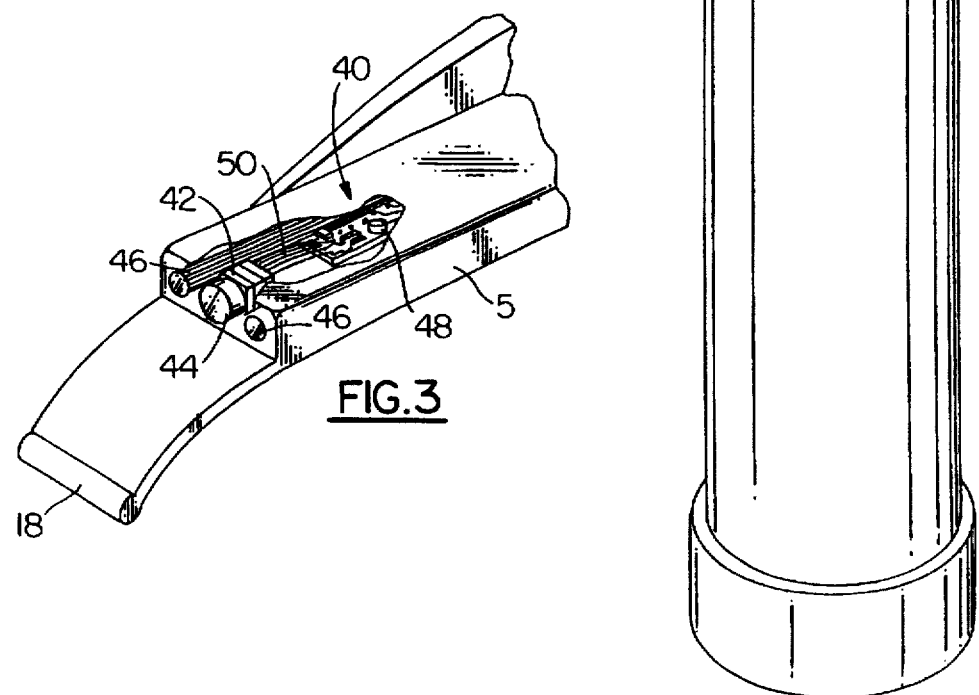
FIG. 3 is a fragmentary perspective view of a laryngoscope according to the invention having a cutaway section showing details of an image sensor assembly.

Referring to additional but nonessential features of typical laryngoscope, with reference to FIG. 2 it is seen that laryngoscope 10 may include mounting formations, e.g. 24, for receiving a handle 20 and a guide 26 normally extending generally perpendicularly from body 12 for guiding insertion of an endotracheal tube into an airway passage.

Elongated body 12 of a laryngoscope according to the invention normally includes at least one elbow or is gradually curved throughout its length to define a convex surface 30 of the laryngoscope and a concave surface of the laryngoscope 32. By way of example, the laryngoscope of FIG. 2 includes a rather pronounced and definite elbow 34, while the laryngoscope 10 of FIGS. 1 and 4 are generally curved throughout their length.

As demonstrated by FIGS. 1, 2, and 4 laryngoscope can be made in a variety of different designs. Laryngoscopes are also made in a variety of different sizes. The choice made by a care provider of the type and size of laryngoscope to use depends of the size and shape of a patient's airway passage, the particular application of the laryngoscope, and the area of tissue in an airway passage which tip 18 is intended to contact.

Regardless of application, tip 18 is adapted to contact a tissue surface at an angle such that a force applied to laryngoscope having a component in a direction along the axis 36 of distal end 14 serves to urge airway passage tissue in a desired direction.

In accordance with one embodiment of the invention, image sensor assembly 40 is mounted on the convex surface of the laryngoscope body and is spaced apart from the distal end (contact surface) of the laryngoscope. A convex surface herein is either a surface including the exterior surface of an elbow, e.g. 34, or is the exterior surface of a gradually curved body, as shown in FIGS. 1 and 4. Because distal end 14 forms an angle with contacted airway passage tissue when in use, it is seen that an image sensor directed tangentially with respect to convex surface 30 will be directed in a direction away from the tissue being contacted and toward a region of interest when the laryngoscope is in use. Mounting image sensor 42 at a spaced apart distance from tip 18 ensures that tissue surrounding the area which tip 18 contacts does not contact lens 44 or does not otherwise interfere with the operation of image sensor assembly 40.

Accordingly, image sensor assembly 40 mounted on convex surface 30 may include an image sensor 42 whose active surface is preferably directed in a direction generally tangential with convex surface 30 at the mounting point of the laryngoscope body on which the assembly is mounted, a lens system 44 for focusing images onto the image sensor 42, illumination elements 46, and may include a circuit board 48 including circuit components for at least partially or preliminarily processing image signals generated image sensor 42. Circuit board 48 may be spaced apart from image sensor 42 and connected to image sensor 42 by way of flexible conductors 50, thereby enabling to image sensor assembly housing 52 to be made of flexible material or to have a curved configuration. Illumination elements may be provided by fiber optic bundles 46 as shown or by another conventional light source, such as a light bulb. Image sensor 42 may be a visible light or infrared (IR) type image sensor in a single element, linear, or matrix array available in various technologies including CCD, CMOS, NMOS, PMOS, CID and CMD technologies. Chord 54 is provided to house various electrical conductors for carrying image data signals from image sensor 42 to an external video processing unit and to transmit various enable and drive pulses to image sensor 42. Chord 54 may also house fiber optic bundles 46 and provide a connection between laryngoscope 10 and a light source of a "light box" containing both video processing circuitry and a light source or else another chord (not shown) may be provided to connect bundles 46 to an independent light source. For good illumination of the area of interest a pair of fiber optic bundles 46 may be disposed on either side of image sensor 42 in image sensor assembly as shown.

In accordance with one embodiment of the invention, track 56 is formed on the convex surface 30 of a laryngoscope body, and housing 52 which houses the image sensor assembly is adapted to be received on the track. Thereby, the distance of the image sensor to a target object is adjusted by moving the image sensor assembly back or forth along the track. It is seen that track 56 may be formed by a pair of rails 58. Preferably, image sensor assembly housing 52 is made so that it can be completely removed from track and reattached on track 56 or to a track of a different laryngoscope. If housing 52 is made to be removably attachable to track 56, then one image sensor assembly can be transferred from one to any number of other laryngoscopes adapted to receive the image sensor assembly housing, thereby saving the cost of including a separate image sensor assembly for each laryngoscope. Imager housing 52 can be made removably attachable on track simply by extending track receiving formations 60 of imager housing 52 to extend to first end 62 or second end 64 imager housing 52.

Of course, track 56, which facilitates sliding adjustment of assembly on surface 30, is not necessary if it is desired only that image sensor assembly 40 be removably attachable to body. Image sensor assembly housing, e.g. 52, can be made removably attachable to laryngoscope body 12 by any number of attachment adaptations providing removable attachment including by way of bolts, screws, pin and hole interlocking fasteners, clamps, latches, microloop-and-hook type fasteners, etc.

Track 56 nevertheless offers advantages over other possible attachment techniques in that track enables sliding adjustment of image sensor assembly housing 52, and does not require small mechanical components which may become dislodged from laryngoscope 10 and fall into a patient's airflow passage. To the end that track 56 is made without small dangerous component parts, housing 52 and track should be formed so that housing 52 is held in a stable position on track 56 by friction forces without use of auxiliary fasteners or stabilization components. Track 56 may comprise any number of rails, and the cross-section of each rail can be of virtually any shape so long as the rail is received or receives a complementary formed formation of image sensor assembly housing 52. Track 56 can be formed to have female shaped rails for example. In one possible embodiment, track 56 can comprise a single slot opening toward surface 30 formed coextensively with surface, and housing 52 can include a pin or screw or series of screws received in the elongated slot.

If track 56 is formed along an elbow, e.g. 34, or along a curved surface of a laryngoscope body as is shown in FIG. 4, and an image sensor assembly housing is complementarily formed so that it is received by the track, then movement of the image sensor assembly housing along track 56 provides two distinct functions. First, movement of housing 52 along track 56 adjusts the distance between an image sensor and a target. Second, as a result of the track being formed on a curved surface, movement of image sensor assembly housing adjusts the angle of orientation of image sensor 42 with respect to axis 36 of distal end 14, and therefore adjust the view field of the image sensor.

In use of the invention, it is common to observe the adequacy of a view field when the laryngoscope is used with the image sensor assembly housing adjusted to a first position, and then to adjust the positioning of the image sensor assembly housing along track 56 alternatively until a desired view field providing adequate viewing of a region of interest is achieved.

While the present invention has been explained with reference to a number of specific embodiments, it will be understood that the spirit and scope of the present invention should be determined with reference to the appended claims.

What is claimed is:

1. A laryngoscope adapted for use in opening an airway passage, said laryngoscope comprising:
   an elongated body having a distal end and a convex surface;
   a tip formed at said distal end adapted for contacting tissue of said airway passage;
   a track formed lengthwise on said convex surface; and
   an image sensor assembly including an image sensor mounted on said track so that sliding of said image sensor assembly on said track adjusts a distance of said image sensor assembly to a target, and adjusts a viewing direction of said image sensor assembly, said track having a length greater than a length of said image sensor assembly so that said track allows positional adjustment of said imaging assembly on said track.

2. The laryngoscope of claim 1, wherein said distal end includes an axis and wherein said image sensor is oriented at an angle with respect to said axis.

3. The laryngoscope of claim 1, wherein said image sensor is spaced apart from said tip.

4. The laryngoscope of claim 1, wherein said image sensor is mounted in a direction generally tangential with said elongated body.

5. The laryngoscope of claim 1, wherein said image sensor assembly further comprises:
   a lens system mounted forwardly of said image sensor toward said distal end; and
   a pair of fiber optic bundles disposed on either side of said image sensor for illuminating a target forward of said image sensor.

6. The laryngoscope of claim 1, wherein said image sensor assembly is lengthwise slidably mounted on said elongated body so that a distance between said image sensor and a target is adjusted by sliding said image sensor assembly.

7. The laryngoscope of claim 1, wherein said elongated body includes an elbow, and wherein said track is formed along said elbow.

8. A laryngoscope adapted for use in opening an airway passage, said laryngoscope comprising:
   an elongated body having a distal end and a convex surface;
   a tip formed at said distal end adapted for contacting tissue of said airway passage; and
   mounting means formed on said convex surface adapted to receive an image sensor assembly of the type including an image sensor, said mounting means including a track formed lengthwise on said convex surface, said track comprising a slot opening toward said convex surface.

9. A laryngoscope adapted for use in opening an airway passage, said laryngoscope comprising:
   an elongated body having a distal end and a convex surface;
   a tip formed at said distal end adapted for contacting tissue of said airway passage;
   mounting means formed on said convex surface adapted to receive an image sensor assembly of the type including an image sensor;
   an image sensor assembly received in said mounting means, said image sensor assembly including
   an image sensor;
   a lens system mounted forwardly of said image senor toward said distal end;
   a pair of fiber optic bundles disposed on either side of said image sensor for illuminating a target forward of said image sensor;
   a circuit board spaced apart from said image sensor; and
   a plurality of flexible conductors interposed between said image sensor and said circuit board providing flexible connection between said image sensor and said circuit board.

* * * * *